United States Patent
Patel et al.

(10) Patent No.: US 8,703,687 B2
(45) Date of Patent: Apr. 22, 2014

(54) CLEAR LIQUID COMPOSITION COMPRISING ALKANOYL GLYCINATE, AMPHOTERIC, ALKYL SULFATE AND SPECIFIC ACRYLATE POLYMERS

(75) Inventors: Rajesh Patel, Middlebury, CT (US); Tirucherai Varahan Vasudevan, Bethany, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 81 days.

(21) Appl. No.: 12/858,578

(22) Filed: Aug. 18, 2010

(65) Prior Publication Data

US 2012/0046210 A1    Feb. 23, 2012

(51) Int. Cl.
*A61K 8/81*    (2006.01)

(52) U.S. Cl.
USPC .......................................... 510/159; 510/123

(58) Field of Classification Search
USPC ......................................................... 510/159
See application file for complete search history.

(56) References Cited

U.S. PATENT DOCUMENTS

| | | | |
|---|---|---|---|
| 6,235,298 B1 * | 5/2001 | Naser et al. | 424/401 |
| 6,533,873 B1 | 3/2003 | Margosiak et al. | |
| 6,939,938 B2 * | 9/2005 | Benard et al. | 528/49 |
| 7,041,627 B2 * | 5/2006 | Kruse et al. | 510/123 |
| 2005/0158351 A1 * | 7/2005 | Soliman et al. | 424/401 |
| 2006/0140897 A1 * | 6/2006 | Patel et al. | 424/70.13 |
| 2008/0138438 A1 * | 6/2008 | Taylor et al. | 424/604 |

OTHER PUBLICATIONS

Co-pending application for Patel et al.; U.S. Appl. No. 12/858,578, filed Aug. 18, 2010, entitled: clear Liquid Composition Comprising Alkanoyl, Glycinate, Amphoteric, Alkyl Sulfate and Specific Acrylate.

Jones, Dr. Charles E., May 1, 2005, Multifunctional Synthetic Rheology Modifers for Personal Care Formulations: More Than Just Thickeners, Cosmetic Science Technology, ., 1-23, US.

Mintel GNPD, Jun. 2008, Intensive Age-Defense Hydrating Foam, Mintel GNPD, ., 1-3, IN.

Mintel GNPD, Nov. 2001, Cleansers, Mintel GNPD, ., 1-2, US.

Rohm and Haas, Apr. 1, 2005, Aculyn 88—more than just a thickener!, Rohm and Haas Personal Care, ., 1-2, US.

PCT Search Report and Written Opinion on PCT Appln. No. PCT/EP2011/063307 dated Jul. 13, 2012.

* cited by examiner

*Primary Examiner* — Nicole M Buie-Hatcher
*Assistant Examiner* — M. Reza Asdjodi
(74) *Attorney, Agent, or Firm* — Ronald A. Koatz

(57) ABSTRACT

The application relates to clear liquid compositions comprising alkanoyl glycinate, amphoteric, alkyl sulfate and specific acrylate polymers.

11 Claims, No Drawings

CLEAR LIQUID COMPOSITION COMPRISING ALKANOYL GLYCINATE, AMPHOTERIC, ALKYL SULFATE AND SPECIFIC ACRYLATE POLYMERS

FIELD OF THE INVENTION

The present invention relates to mild isotropic liquid compositions comprising specific glycinate, amphoteric, alkyl sulfate systems of defined pH. Specifically, it relates to use of specific associative acrylate polymers to ensure the compositions are viscous, clear (an important consumer perceived attribute for isotropic body wash formulations) and mild.

BACKGROUND

Isotropic liquid formulations are commonly used as shampoo and/or liquid skin cleanser compositions. These compositions comprise surfactant systems which function, among other things, as cleanser component. One particular surfactant system which can be used comprises a combination of alkanoyl glycinate surfactant, amphoteric surfactant and alkyl sulfate surfactant (e.g., alkoxylated or non-alkoxylated alkyl sulfates).

A desirable characteristic of some isotropic liquid cleanser is that they be both viscous and clear to the consumer. This can be difficult to accomplish due to the presence of fatty acids, salts, final formulation pH, fragrance solubility and choice of polymers used.

Unexpectedly, applicants have found specific polymers or combinations of polymers that provide clarity and mildness for isotropic bodywash (BW) formulations having specific surfactant systems and falling within a defined pH range.

More specifically, applicants have now found that, when specific acrylate polymers are used in the specific surfactant systems noted above, applicants can provide mild, viscous, clear compositions noted. Clarity is defined as per the protocol section below.

Applicants are aware of no art which recognizes the criticality of specific acrylate polymers to provide viscosity, clarity, and mildness in the specifically claimed systems of the invention.

BRIEF DESCRIPTION OF THE INVENTION

The present invention provides mild, viscous, clear isotropic compositions (isotropic composition are typically liquid compositions which comprises dispersion of spherical and/or rod micelles rather than an ordered liquid crystalline phase which characterizes lamellar dispersions). Isotropic compositions tend to have lower zero shear viscosities and typically require use of some external structurant, especially if they will be suspending particles of any kind. Typically, isotropic body wash compositions are not mild due to the choice of surfactants used to achieve viscosity and clarity. Preferred systems of our invention are also particle suspending.

In particular, the invention relates to isotropic liquids having specific glycinate, amphoteric and alkyl sulfate surfactant systems. Typically, such isotropic compositions comprising an external structurant will have an opaque (non-clear) appearance. The higher the desired zero-shear viscosity of the liquid, the more structurant is typically used. However, use of structurant (to obtain desired viscosity) would generally be expected to render compositions more opaque.

Unexpectedly, applicants have found that if specific acrylate polymers are used and compositions are maintained within defined pH range (about 6.5 to 7.5), not only is it possible to achieve desired viscosities, but the isotropic compositions are also clear. The specific compositions of the invention are also, as noted, mild (e.g., they have low lower visual dryness and erythema scores compared to similar products in the market). Thus, the unexpected combination of this specific surfactant system in defined pH range and specific acrylate polymers provides a clear, isotropic solution, preferably one with viscosity high enough to be capable of particle suspension.

Specifically, the invention comprises compositions comprising:
(a) 2 to 7%, preferably 2.5 to 5% by wt. alkanoyl glycinate;
(b) 1 to 5%, preferably 2 to 4% by wt. of an amphoteric and/or zwitterionic surfactant;
(c) 1 to 5%, preferably 1.5 to 3% by wt. alkyl sulfate; and
(d) specific associative polymers, which are amphiphilic polymers comprising both hydrophilic units (e.g., acrylate or methacrylate) and hydrophobic units (e.g., at least one $C_8$ to $C_{30}$ fatty chain);

wherein compositions have viscosity of 5 to 25 thousand, preferably 8500 to 20 thousand centipoise (cps); measured using Brookfield Viscometer, Spindle 5, at shear rate of 20 rpm at 25° C. (shearing typically for about one minute) and wherein compositions have clarity value, as defined, of 4 or 5. Further pH of composition should be about 6.5 to 7.5, preferably 6.8 to 7.3, more preferably 6.8 to 7.2 to ensure clarity of formulation.

In some embodiments, compositions may further comprise low levels (e.g., 0.1-2%, preferably 0.5 to 1.5% by wt.) of alkali metal acyl isethionate (e.g., sodium cocoyl isethionate). Further, compositions of the invention preferably comprise from about 0.1 to 3%, preferably 0.2 to 2% by wt. free fatty acid.

The associative polymers of the invention are water-soluble polymers containing non-polar groups (e.g., fatty chain) which gather together in aggregates in polar media (e.g., water). Such associative polymers are capable of reversibly combining with each other or with other molecules. By contrast, applicants have found that non-associative polymers are not capable of providing clarity and viscosity values in the specific compositions of the invention (defined both by surfactant systems and by pH range).

As noted, the polymers of the invention preferably are specifically acrylate and/or methacrylate (e.g., skeleton comprising predominately hydrophilic groups) with attached fatty chain hydrophobic groups.

Preferably, the total surfactant content of composition is 10% by wt. or less, e.g., 1 to 10%, preferably 2 to 9% total.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental example, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y" it is understood that all ranges combining the different endpoints are also contemplated. Further in specifying the range of concentration, it is noted that any particular upper concentration can be associated with any particular lower concentration. Where the term "comprising" is used in the specification or claims, it is not intended to exclude any terms, steps or features not specifically recited. For the avoidance of doubt, the word "comprising" is intended to mean "including" but not necessarily "consisting of" or "composed of". In other words, the listed steps, options, or alternatives need not be exhaustive. All temperatures are in degrees Celsius (° C.) unless specific otherwise. All measurements are in SI units unless specified otherwise. All documents cited are—in relevant part—incorporated herein by reference.

DETAILED DESCRIPTION OF THE INVENTION

The present invention relates to mild (e.g. measured by lower visual dryness and erythema scores relative to marketed mild products), viscous, clear isotropic liquid compositions. The compositions comprise a specific, desirable combination of surfactants and specific acrylate polymers (e.g., specific associative polymers). The compositions are also within a defined pH range.

More particularly, most isotropic liquids require some polymers (e.g., thickening agent) to help enhance zero-shear viscosity. Use of such polymers, for example, acrylate polymers, typically result in isotropic compositions which are opaque (not clear). As noted above, it is typically difficult to control opaqueness due to presence of fatty acids, salts, formulation pH, and polymer choice. It is unpredictable that particular acrylate polymers in particular systems would provide such clear systems. In compositions originally prepared by applicants, the formulations were in fact opaque or, if they provided greater clarity, they did not provide desirable viscosities (e.g., 5,000 to 25,000, preferably 8500 to 20 thousand cps measured using Brookfield viscometer, with Spindle 5, SP5, at shear rate of 20 rpm at 25° C.). Further, it was not apparent that clear formulations could be formed at all using the combination of specific surfactants of our invention, particularly since, for example, polymers are required to provide minimum viscosity and such polymers, as noted, are associated with opaqueness.

Unpredictably, applicants have found that specific acrylate polymers provide both clarity and adequate viscosity in the specific surfactant systems of our invention (used within a defined pH range).

The composition of the invention comprises:
(a) 2 to 7%, preferably 2.5 to 5% by wt. alkanoyl glycinate;
(b) 1 to 5%, preferably 2 to 4% by wt. of an amphoteric and/or amphophilic surfactant;
(c) 1 to 5%, preferably 1.5 to 3% by wt., alkyl sulfate; and
(d) associative polymer which comprises hydrophilic backbone and at least one attached hydrophobic unit; particularly hydrophilic unit comprising unsaturated carboxylic acid or derivative (e.g., acrylate and/or methacrylate) and hydrophobic unit which is $C_8$ to $C_{30}$ alkyl ester or oxyethylenated $C_8$ to $C_{30}$ alkyl ester of unsaturated carboxylic acid,
wherein total % by wt. of surfactant is preferably 10% by wt. or less
wherein viscosity of the composition is:
5 to 25 thousand, preferably 8500 to 20 thousand cps (using Brookfield SP5 viscometer at 20 RPM at 25° C., typically measured after about one minute of shear);
most preferably, viscosity is from about 10,000 to 17,000 cps; and
wherein the composition has clarity value of 4 or 5 on a scale of 1 to 5, as measured in test defined in protocol section;
and wherein pH of the composition is 6.5 to 7.5, preferably 6.8 to 7.3, more preferably 6.8 to 7.2.

The rheology modifier is an associative thickener and, preferably should be an efficient on particle suspender in high viscosity formulation (e.g., greater than or equal to 8.5 thousand cps as noted above).

The surfactant system of the invention is defined in more detail below:

A first requirement of the surfactant system is that it comprises 1 to 6%, preferably 2 to 5%, more preferably 3-5% by wt. of a salt of alkanoyl glycinate. Preferred salts include alkali metal salts of alkanoyl glycinate such as sodium cocoyl glycinate and/or alkanolamino salts such as trialkanolamine salt of glycinate.

As is well know in the art, alkanoyl is the systematic name for group:

which is also known as an acyl group. Thus, alkanoyl glycinate is the same as acyl glycinate and represents a molecule, for example, where salt of acyl group, such as for example:

(where R may be, for example, $C_8$-$C_{24}$, preferably $C_{12}$-$C_{20}$) is combined with glycine:

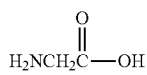

to form the alkanoyl glycinate (an amide where alkanoyl group bonds to nitrogen to form amide):

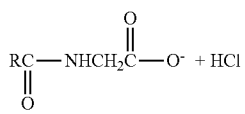

The above reaction may be conducted, for example, by an acid chloride route where R group on the acyl chloride is used to define the R group on the final alkanoyl glycinate (e.g., cocoyl glycinate if R in the acyl group is a cocoyl group).

A second required component of the surfactant system is the inclusion of amphoteric and/or zwitterionic surfactants (defined collectively as "amphoteric surfactant" or "amphoteric lathering surfactant"). These may be used in an amount of from 1 to 5%, preferably 2% to 4% by wt of the composition.

As indicated, the term "amphoteric surfactant" as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American Edition (1986), published by Allured Publishing Corporation; and McCutcheon's, Functional Materials, North American Edition (1992); both of which are incorporated by reference herein in their entirety.

Non-limiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonaine 16SP from Lonza Corp.), lauryl bis-(2-hydroxyethyl)carboxymethyl betaine, oleyl dimethyl gamma-carboxypropyl betaine, lauryl bis-(hydroxypropyl)alpha-carboxyethyl betaine, coco dimethyl sulfopropyl betaine, lauryl dimethyl sulfoethyl betaine, lauryl bis-(2-hydroxyethyl)sulfopropyl betaine, amidobetaines and amidosulfobetaines (wherein the RCONH(CH$_2$)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Example of sultaines and hydroxysultaines include materials such as cocamidopropyl hydroxysultaine (available as Miratane CBS from Rhone-Poulenc).

Preferred for use herein are amphoteric surfactants having the following structure:

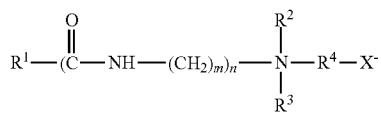

wherein R$^1$ is unsubstituted, saturated or unsaturated, straight or branched chain alkyl having from about 9 to about 22 carbon atoms. Preferred R$^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably abort a3; n is either 0 or 1, preferably 1; R$^2$ and R$^3$ are independently selected from the group consisting of alkyl having from 1 to about 3 carbon atoms, unsubstituted or mono-substituted with hydroxy, preferred R$^2$ and R$^3$ are CH$_3$; X is selected form the group consisting of CO$_2$, SO$_3$ and SO$_4$; R$^4$ is selected form the group consisting of saturated or unsaturated, straight or branched chain alkyl, unsubstituted or mono-substituted with hydroxy, having from 1 to about 5 carbon atoms. When X is CO$_2$, R$^4$ preferably has 1 to 3 carbon atoms, more preferably 1 carbon atom. When X is SO$_3$ or SO4, R$^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine);

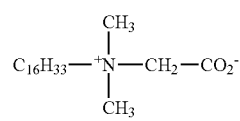

Cocamidopropylbetaine

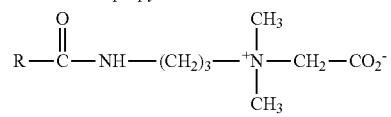

Cocamidopropyl hydroxy sultaine wherein R has from about 9 to about 13 carbon atoms

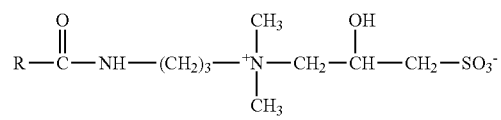

wherein R has from about 9 to about 13 carbon atoms.

A third requirement of the surfactant system is use an alkyl sulfate, which includes alkyl and alkyl ether sulfate. These typically have respective formulae ROSO$_3$M and RO(C$_2$H$_4$O)$_x$SO$_3$M, where R is alkyl or alkenyl of about 10 to 30 carbon atoms; x is from about 1 to 10; and M is a water soluble cation such as ammonium, sodium, potassium, magnesium and triethanolamine, A preferred surfactant is alkali metal ether sulfate such as alkoxylated or non-alkoxylated sodium lauryl ether sulfate.

The alkyl sulfate is used in an amount of 1 to 5%, preferably 1.5 to 3% by wt.

In some preferred embodiments, compositions of the invention will comprise 0.1-3%, preferably 0.1 to 2%, more preferably 0.5 to 1.5% by wt. alkali metal acyl isethionate, e.g., sodium cocoyl isethionate. These are typically formed from a combination of alkali metal salts of isethionate (e.g., HO—CH$_2$—CH$_2$SO$_3$Na) and fatty acid or oils such as coconut oils. Other preferred compositions comprise 0.1 to 3%, preferably 0.2-2% but free fatty acids (C$_8$-C$_{24}$ fatty acids, preferably C$_{14}$-C$_{20}$ fatty acids or mixtures thereof).

A fourth requirement of the invention is that the compositions have suspending polymer which is able to provide sufficient viscosity (e.g., to suspend particles), but which simultaneously provides clarity (as defined) in the alkanoyl glycinate, amphoteric, alkyl sulfate system of the invention. Specific acrylate polymers are contemplated for the invention.

Polymers of the invention must be "associative polymers". Such polymers are amphiphilic polymers comprising both hydrophilic units and hydrophobic units, for example, at least one C$_8$ to C$_{30}$ fatty chain and at least one hydrophilic unit. Associative polymers are capable of reversibly combining with each other or with other molecules. In particular, the polymers should be anionic amphiphilic polymers.

The anionic amphiphilic polymers comprising at least one hydrophilic unit and at least one fatty-chain unit, may, for example, be chosen from those comprising at least one fatty-chain length allyl ether unit and at least one hydrophilic unit comprising an ethylenic unsaturated anionic monomeric unit, for example, a vinyl carboxylic acid unit and further, for example, chosen from units derived from acrylic acids, methacrylic acids and mixtures thereof, wherein the fatty-chain allyl ether unit corresponds to the monomer of formula below:

$$CH_2=CR_1CH_2OB_nR$$

in which $R_1$ is chosen from H and $CH_3$, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and further, for example, form 10 to 24 carbon atoms and even further, for example, from 12 to 18 carbon atoms.

The anionic amphiphilic polymers may further be chosen, for example, from those comprising at least one hydrophilic unit of unsaturated olefinic carboxylic acid type, and at least one hydrophobic unit of the type such as a ($C_8$-$C_{30}$) alkyl ester or ($C_8$-$C_{30}$) oxyethylenated alkyl ester of an unsaturated carboxylic acid. The hydrophilic unit of unsaturated olefinic carboxylic acid type corresponds to, for example, the monomer of formula below:

$$CH_2=C(R_1)COOH$$

in which $R_1$ is chosen from H, $CH_3$, $C_2H_5$ and $CH_2COOH$, i.e. acrylic acid, methacrylic, ethacrylic and itaconic acid units. And the hydrophobic unit of the type such as a ($C_8$-$C_{30}$) alkyl ester or ($C_8$-$C_{30}$) oxyethylenated alkyl ester of an unsaturated carboxylic acid corresponds to, for example, the monomer of formula below:

$$CH_2=(R_1)COOB_nR_2$$

in which $R_1$ is chosen from H, $CH_3$, $C_2H_5$ and $CH_2COOH$ (i.e., acrylate, methacrylate, ethacrylate and itaconate units), B is an ethyleoxy radical, n is chosen from zero and integers ranging from 1 to 100, $R_2$ is chosen from $C_8$-$C_{30}$ alkyl radicals, for example, $C_{12}$-$C_{22}$ alkyl radical.

Representative anionic amphiphilic polymers that can be used may further be cross-linked.

The cross-linking agent can be a monomer comprising a group (IV)

$$CH_2=C<$$

with at least one other polymerizable group whose unsaturated bonds are not conjugated with respect to one another. Mention may be made, for example, of polyallyl ethers such as polyallylsucrose and polyallyl pentaerythritol.

Preferable associative polymeric thickeners for use herein comprise at least one hydrophilic unit which is unsaturated carboxylic acid or its derivative, and at least one hydrophobic unit which is a $C_8$-$C_{30}$ alkyl ester or oxyethylenated $C_8$-$C_{30}$ alkyl ester of unsaturated carboxylic acid. The unsaturated carboxylic acid is preferably acrylic acid, methacrylic acid or itaconic acid. Examples can be made of material sold under trade name Aculyn® 88 by the company Rohm & Haas, materials sold under trade names Permulen TR1, Carbopol 2020, Carbopol Ultrez-21 by the company Noveon, and materials sold under the trade names Structure 2001 and Structure 3001 by the company National Starch.

Specifically, preferred cross-polymers may be found under INCI description of acrylate/steareth-20 methacrylate cross-polymer or acrylate/$C_{10}$-$C_{30}$ alkyl acrylate cross-polymer. An example of acrylate/stearath-20 methacrylate cross polymer is Aculyn®88 from Rohm & Haas which is a synthetic polymer that blends stearath-20 with one or more forms of methacrylic acid. An example of acrylate $C_{10}$-$C_{30}$ alkyl acrylate is Carbopol® Ultrez 20 polymer from Lubrizol or Carbopol® EDT 2020 polymer, also from Lubrizol.

These polymers were able to achieve viscosity measured in Brookfield SP5 viscometer (e.g., using Spindle 5) measured at 20 RPM (25° C.) of 5000 to 25,000, preferably 8500 to 20,000, more preferably 10,000 to 17,000 cps.

Further, they are able to maintain viscosity of 4 or 5 on a scale of 1-5 measured as described in protocol.

In addition, pH of the composition is 6.5 to 7.5, preferably 6.8 to 7.3.

In a preferred embodiment, composition of the invention may comprise a skin compatible oil which may include ester oils, silicone oils or mixtures thereof.

Ester oils may include fatty acid mono and polyesters such as cetyl octanoate, myristyl lactate, isopropyl myristate, glycerol mono- or distearate, sucrose ester, sorbitol ester or the like. It may also include triglycerides and modified triglycerides including vegetable oils such as jojoba, soybean, canola, etc.

Liquid hydrocarbons include linear and branched oils such as liquid paraffin, squalene, mineral oil and petrolatum.

Another oil which may be used is silicone based oil. This includes linear and cyclic polydimethyl siloxane, organo functional silicones and amino silicones.

Oils may comprise 0.1 to 15%, preferably 0.5 to 10%, more preferably 0.5 to 5% by wt. of the composition.

The aqueous compositions preferably comprise at least 60%, more preferably greater than 65% by wt. water.

The aqueous phase may further comprise hydrophilic moisturizer which may include polyols such as alkylene glycols, sorbitol or glycerin. Polymeric polyols such as polypropylene or polyethylene glycol may also be used.

Other ingredients typically found in liquid formulations may be used.

These include (without limitation) auxiliary thickeners (e.g., carboxymethyl cellulose); perfumes, sequestering agents; cooling agents; opacifiers and pearlizers (e.g., titanium dioxide).

Other optionals include antimicrobial agents, preservatives (e.g., parabens), suds boosters (e.g., coconut acyl mono or diethanolamides); antioxidants; cationic conditioning polymers (e.g., Merquat® type polymers); exfoliates; ionizing salts; organic acids (e.g., citric or lactic acid).

Protocol

Clarity—to measure clarity, the various solutions were prepared and then transferred to two ounce (size of bottle not a criticality) clear, glass bottles. Employees were then asked to evaluate the clarity on a scale of 1 to 5 with 1 being most turbid and 5 being completely clear.

Viscosity measurements were concluded on SP5 Brookfield Viscometer as noted above.

Mildness

The cleansing products were tested in an exaggerated 2 day wash procedure. Products were randomly applied to the forearms of 15 subjects six times a day for two days. 0.2 ml of product was applied with a moistened cloth towel to a 9 cm2 area of skin. During each wash, the product was in contact with the skin for 1 minute and 40 seconds prior to rinsing for 15 seconds. Visual grading of dryness and erythema was assessed at baseline and 2 hours after the last wash on day 2 (endpoint) using a published grading scale from Lukacovic reference[1], said reference hereby incorporated by reference into the subject application.

[1] Lukacovic, M. F., Dunlap, F. E., Michaels, S. E., Visscher, M. O. and Watson, D. D. forearm wash test to evaluate the mildness of cleansing products. J. Soc. Cosmet. Chem. 39, 355-366 (1988)

EXAMPLES

The following examples in Table 1 were prepared together with viscosity and clarity measurements for each.

TABLE 1

| Ingredient (% by wt.) | A | B | C | D | E | F | G | H | I | Ex 1 | Ex 2 | Ex 3 | Ex. 4 |
|---|---|---|---|---|---|---|---|---|---|---|---|---|---|
| SLES (a) | 2 | 2 | 2 | 2.5 | 2 | 3 | 3 | 3 | | 2 | 2 | 3 | 3 |
| NaCG (b) | 3 | 3 | 3 | 4 | 5 | 5 | 5 | 3 | 3 | 5 | 3 | 3 | 5 |
| CAPB (c) | 2 | 2 | 3 | 2.5 | 3 | 2 | 3 | 3 | 3 | 2 | 3 | 2 | 3 |
| Polymer @1.5% | (d) | (e) | (d) | (e) | (e) | (d) | (e) | (e) | (f) | (f) | (f) | (f) | (f) |
| Viscosity (g) | 300 | 620 | 620 | 840 | 1040 | 1260 | 1420 | 1520 | 2280 | 9420 | 11320 | 11600 | 15000 |
| Clarity | 3 | 4 | 2 | 5 | 5 | 3 | 5 | 5 | 3 | 4 | 5 | 5 | 5 |

Clarity: 1 = Turbid; 5 = clear (measured on scale of 1-5 as per protocol)
Viscosity: Brookfield SP5, speed 20 revolution per minute (RPM), 25° C.
Amounts in columns are in percent by weight.
(a) sodium lauryl ether sulfate
(b) sodium cocoyl glycinate
(c) cocoamidopropyl betaine
(d) non-associative acrylates/vinyl neodecanoate cross-polymer (Aculyn ® 38 from Rohm & Haas)
(e) non-associative acrylates copolymer (Carbopol Aqua ® SF-1 from Lubrizol)
(f) associative acrylates/steareth 20 methacrylate cross-polymer (Aculyn ® 88 from Rohm & Haas)
(g) Viscosity: Brookfield SP5, speed 20 revolution per minute (RPM) at 25° C.

As seen from Table 1, it is not at all predictable which thickening polymer, or even which acrylate polymer, will provide the required viscosity and clarity (clear composition is desired by consumers) in specific glycinate, amphoteric, alkyl sulfate system. Only associative polymer had desired viscosity and clarity.

The following additional examples were prepared as set forth in Table 2 below.

As seen, a non-associative acrylates/vinyl neodecanoate cross-polymer (e.g., an Aculyn® 38 polymer from Rohm & Haas) provides compositions with very low viscosities and unacceptable clarity (see Comparatives A & C in first table). While not wishing to be bound by theory, this is believed to be the case because the polymer is non-associative.

A chemically non-associative acrylates co-polymer (e.g., Aqua SF-1® Carbopol polymer from Lubrizol) provides

TABLE 2

| Ingredient | J | Ex. 5 | Ex. 6 | Ex. 7 | Ex. 8 | Ex. 9 | Ex. 10 | K | Ex. 11 | Ex. 12 | Ex. 13 |
|---|---|---|---|---|---|---|---|---|---|---|---|
| Sodium lauryl ether sulfate 1EO | 2 | 2 | 2 | 2 | 2 | 2 | 3 | 3 | 3 | | 2 |
| Na cocoylglycinate | 3 | 3 | 3 | 3 | 3 | 3 | 2 | 2 | 2 | 3.5 | 3 |
| CAPB | 3 | 3 | 3 | 3 | 3 | 3 | 3 | 3 | 3 | | 3 |
| Na Lauryl Amphoacetate | | | | | | | | | | 3.5 | |
| Sodium cocoyl isethionate | | 1 | 1 | 1 | 1 | 1 | 1 | 1 | 1 | | 1 |
| Stearic Acid | .31 | .31 | .31 | .31 | .31 | .31 | .31 | .31 | .31 | | .31 |
| Lauric Acid | .25 | .25 | .25 | .25 | .25 | .25 | .25 | .25 | .25 | 1 | .25 |
| (a) | 1.75 | | | | | | | | | | |
| (b) | | | | 0.8 | | .16 | | | 0.4 | | |
| (c) | | | .8 | | .16 | | | | | 1.0 | 0.8 |
| Glycerol | 1 | 1 | 1 | 1 | 1 | 1 | 1 | 1 | 1 | 1 | 1 |
| Aculyn 88 (100%) | | .80 | | | .65 | .65 | .75 | .75 | 0.25 | | |
| Snowhite PJ (petroleum jelly) | | | | | | | | | | | 2.0 |
| Preservative | 0.3 | 0.3 | 0.3 | 0.3 | 0.3 | 0.3 | 0.3 | 0.3 | 0.3 | 0.3 | 0.3 |
| Fragrance | 1.0 | 1.0 | 1.0 | 1.0 | 1.0 | 1.0 | 1.0 | 1.0 | 1.0 | 1.0 | 1.0 |
| pH | 6.8-7.2 | 6.8-7.2 | 6.8-7.2 | 6.8-7.2 | 6.8-7.2 | 6.8-7.2 | 6.8-7.2 | 6.3 | 6.8-7.2 | 6.2-7.2 | 6.8-7.2 |
| Viscosity (CPS) Brookfield, SP5, speed 20 | 500 | 8900 | 14200 | 5900 | 16740 | 8560 | 14880 | 10500 | 11920 | 9800 | 8900 |
| Appearance | Mlky white | Clear | Clear | Clear | Clear | Clear | Clear | Opaque | Clear | Clear | Clear |

(a) Same as polymer (e) from previous Table (Carbopol Aqua ® SF-1 from Lubrizol)
(b) Acrylate $C_{10}$-$C_{30}$ alkyl acrylate associative polymer (Carbopol ® EDT 2020 from Lubrizol)
(c) Acrylate $C_{10}$-$C_{30}$ alkyl acrylate associative polymer (Carbopol ® Ultrez 20 from Lubrizol)

Observations:
Composition Example J with acrylate, non-associative polymer shows low viscosity and opaque appearance
Ex. 5-10 show clear formulation with associative polymer and correct pH range. Further ETD 2020 (Example 7) and Ultrez 20 (Ex. 6) are used in sufficient amounts (e.g., >0.5%, preferably >0.7%) to suspend particles/beads
Ex. 10 versus Comparative K shows difference in pH (6.8-7.2 versus 6.3) and resulting opaqueness
Ex. 12 shows alternative amphoteric surfactant
Ex. 13 is example showing compositions of invention further comprising oil (i.e., petroleum jelly)

some compositions of acceptable clarity (see Comparative D, E, G and H in first table), but all have very low viscosities. Again while not wishing to be bound by theory, this may be because the polymer is not a cross-polymer and/or because it is, as noted, chemically not associative.

In Examples 1 to 4 and 5 to 13 by contrast, it can be seen that the polymer (e.g., Aculyn 88, Carbopol EDT 2020 or Carbopol Ultrez 20) is an associative polymer which is a cross-polymer of acrylic polymer and Stearath 20. The structure of such polymer is built by polymer chain entanglement and an association of hydrophobic groups with surfactants, fatty materials, oils, particles or other hydrophobic groups.

Together, the cross-linked polymer chain allows for sufficient build of low shear viscosity which enable good suspension.

It is noted in Comparative Example I that cross-polymers of the invention do not necessarily work in different surfactant system (e.g., where no SLES is present, as is required by claims of our specific surfactant systems).

Mildness

Examples 8, 13 and Comparatives L and M

To show mildness of the liquid composition of the invention applicants tested examples 8 and 13 as set forth in Table 2 above against two marketed bodywash products with the following formulation:

Product L: Marketed Bodywash: Nivea Happy Time Cream Shower

Ingredients: water, sodium laureth sulfate, cocamidopropyl betaine, PEG 7 glyceryl cocoate, fragrance, *butyrospermum parkii* (shea butter), *helianthus annuus* (sunflower) seed oil, *Prunus Amygdalus* (sweet almond) oil, glycerin, glycol distearate, PEG 40 hydrogenated castor oil, polyquaternium 7, styrene/acrylates copolymer, laureth 4, PEG 90 glyceryl isostearate, PEG 200 hydrogenated glyceryl palmate, laureth 2, citric acid, sodium benzoate, sodium salicylate, ext yellow 7, yellow 6.

Product M: Marketed Bodywash: Dove current revive-EU

Ingredients: aqua, sodium laureth sulfate, glycerin, cocamidopropyl betaine, cocamide MEA, parfum, isopropyl palmitate, *punica granatum* fruit juice, *lippia citriodora* flower/leaf/steamwater, acrylates cipolymner, guar hydroxypropyltrimonium chloride, tocopherol acetate, lactic acid, glycol distearate PEG 40-hydrogenated castor oil, trideceth-9, PPG 12, laureth-4, sodium chloride, citric acid, disodium EDTA, benzopheone-4, sodium benzoate, potassium sorbate, butylphenyl methylpropiopional, citronellol, geraniol, hexyl cinnamal, limonene, linalool, C117200

Mildness tests (for visual dryness and erythema) were conducted as noted in the protocol.

A table showing two day endpoint results (lower numbers being less drying) for Examples 8, 13 and for two products L & M is set forth below:

TABLE 3

| | Average Visual Dryness 2 day endpoint | Average Visual Erythema 2 day endpoint |
|---|---|---|
| Current Dove (Product M) | 1.0 | 0.700 |

TABLE 3-continued

| | Average Visual Dryness 2 day endpoint | Average Visual Erythema 2 day endpoint | |
|---|---|---|---|
| Ex. 8 (clear glycinate) | 0.433 | 0.067 | ↑ More drying more irritating |
| Nivea (Product L) | 0.30 | 0.067 | |
| Ex. 13 (clear glycinate with PJ) | −0.100 | 0.000 | |

As seen from the Table, composition 8 of invention was milder (less drying) than current Product M formulation and comparable to Product L. The formulation with additional PJ was milder (showed an improvement in drying) than all other formulations (the PJ formulation was not significantly different than Nivea with regard to erythema scores). The two inventive compositions are thus clear, mild compositions comprising surfactant systems as set forth.

The invention claimed is:

1. The composition of the invention comprises:
   (a) 2 to 7% by wt. alkanoyl glycinate;
   (b) 1 to 5% of an amphoteric and/or zwitterionic surfactant;
   (c) 1 to 5% by wt. alkyl sulfate; and
   (d) associative polymer comprising unsaturated carboxylic acid or derivative and hydrophobic unit which is $C_8$ to $C_{30}$ alkyl ester or oxyethlenated $C_8$-$C_{30}$ alkyl ester of unsaturated carboxylic acid,
   wherein viscosity of the composition is:
   5 to 25 thousand cps, measured using Brookfield SP5 viscometer at 20 RPM, at 25° C.;
   wherein the composition has clarity value of 4 or 5 on a scale of 1 to 5, as measured in defined clarity test; and
   wherein pH of the composition is 6.5 to 7.5.

2. A composition according to claim 1, wherein viscosity is 8500 to 20,000 cps.

3. A composition according to claim 1 having 10% by wt. or less surfactant.

4. A composition according to claim 1, wherein alkanoyl glycinate is alkali metal cocoylglycinate.

5. A composition according to claim 1, wherein amphoteric is cocoamidopropyl betaine and/or amphoacetate.

6. A composition according to claim 1, wherein said associative polymer further comprises a cross-linking agent.

7. A composition according to claim 1 comprising 2.5 to 5% alkanoyl glycinate.

8. A composition according to claim 1 wherein the pH is 6.8 to 7.3.

9. A composition according to claim 1 additionally comprising 0.1 to 3% by wt. alkali metal acyl isethionate.

10. A composition according to claim 1 comprising an oil.

11. A composition according to claim 10 wherein said oil is petroleum jelly.

* * * * *